US009717907B2

(12) United States Patent
Karunasiri

(10) Patent No.: US 9,717,907 B2
(45) Date of Patent: Aug. 1, 2017

(54) RADIO FREQUENCY ("RF") POWER LEVEL MANAGEMENT SYSTEMS AND METHODS FOR USE IN A COCHLEAR IMPLANT SYSTEM

(71) Applicant: ADVANCED BIONICS AG, Staefa (CH)

(72) Inventor: R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,026

(22) PCT Filed: Dec. 23, 2013

(86) PCT No.: PCT/US2013/077596
§ 371 (c)(1),
(2) Date: Mar. 22, 2016

(87) PCT Pub. No.: WO2015/099682
PCT Pub. Date: Jul. 2, 2015

(65) Prior Publication Data
US 2016/0220818 A1    Aug. 4, 2016

(51) Int. Cl.
*A61N 1/36* (2006.01)
*A61N 1/378* (2006.01)

(52) U.S. Cl.
CPC ....... *A61N 1/36032* (2013.01); *A61N 1/3787* (2013.01)

(58) Field of Classification Search
None
See application file for complete search history.

(56) References Cited

U.S. PATENT DOCUMENTS

| 4,592,359 A | 6/1986 | Galbraith |
| 9,008,787 B2 * | 4/2015 | Carter ................ A61N 1/36032 607/13 |

FOREIGN PATENT DOCUMENTS

| WO | WO-00/00251 | 1/2000 |
| WO | WO-2011/033489 | 3/2011 |

OTHER PUBLICATIONS

International Search Report and Written Opinion received in International Application No. PCT/US13/077596, dated Sep. 25, 2014.

* cited by examiner

*Primary Examiner* — Brian T Gedeon
(74) *Attorney, Agent, or Firm* — ALG Intellectual Property, LLC

(57) ABSTRACT

An exemplary system may include a sound processor that provides radio frequency (RF) power and a cochlear implant that operates in accordance with the RF power. The cochlear implant may include a positive current source and a negative current source that may be electrically coupled to an electrode by way of a common node. The sound processor may 1) direct the cochlear implant to concurrently enable the positive and negative current sources in order to generate a current that has a first predetermined current level and that flows though the positive and negative current sources from a positive voltage supply to a negative voltage supply without providing stimulation to the electrode in a manner perceptible to the patient, and 2) determine a power level of the RF power that is required to generate the current having the first predetermined current level. Corresponding apparatuses and methods are also described.

19 Claims, 7 Drawing Sheets

US 9,717,907 B2

RADIO FREQUENCY ("RF") POWER LEVEL MANAGEMENT SYSTEMS AND METHODS FOR USE IN A COCHLEAR IMPLANT SYSTEM

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

In a typical cochlear implant system, a cochlear implant operates in accordance with radio frequency ("RF") power inductively provided by an externally located sound processor. It is often desirable to minimize the amount of RF power that is provided to the cochlear implant so that battery life of the sound processor may be maximized. To this end, the sound processor may perform an RF power level and internal loading sequence during which a table (e.g., a power estimator ("POEM") table) is built that defines RF power levels required to apply different current levels to a particular electrode. During this RF power level and internal loading sequence, the cochlear implant may use a multiplexer to create a load that is parallel to an electrode and that simulates an impedance associated with the electrode. Current generated by a current source associated with the electrode may then be applied to the load. While the current is being applied, the sound processor may determine an RF power level required to generate and apply the current. Unfortunately, because the electrode is in parallel with the load created by the multiplexer, some of the current is also applied to the electrode. This may result in the patient perceiving a pulsing noise, which can be annoying and/or disconcerting to the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
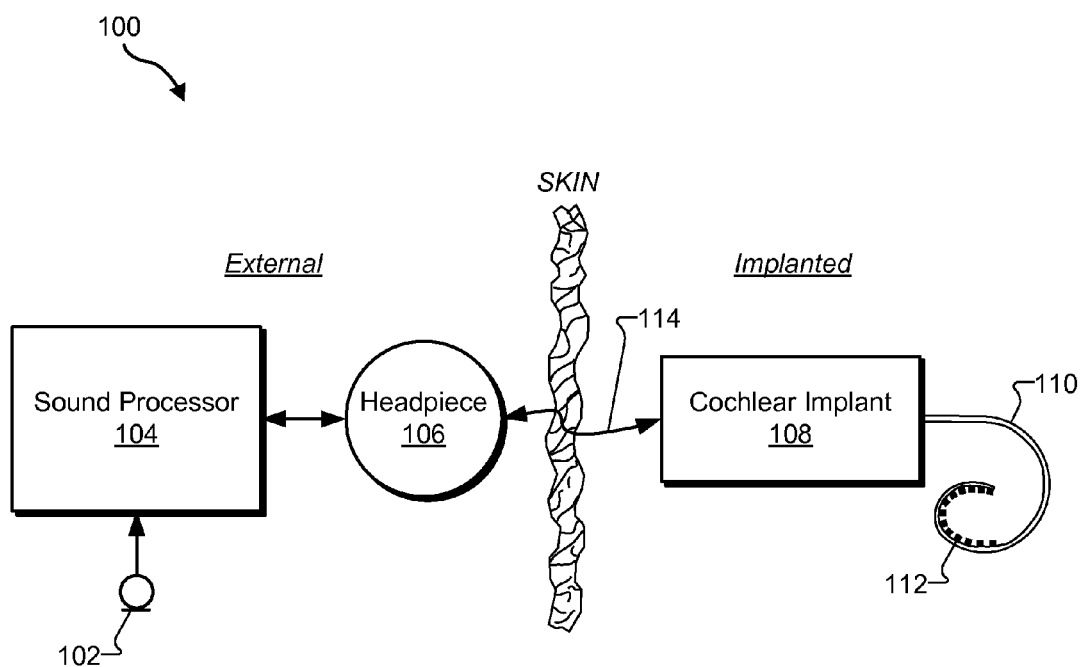
FIG. 1 illustrates an exemplary cochlear implant system according to principles described herein.

RF power level management systems and methods for use in a cochlear implant system are described herein. As will be described in more detail below, a cochlear implant system associated with a patient may include a sound processor that provides RF power and a cochlear implant that operates in accordance with the RF power provided by the sound processor. The cochlear implant may be implanted within the patient and may be electrically coupled to a plurality of electrodes. For each electrode, the cochlear implant may include a positive current source tied to a positive voltage supply and a negative current source tied to a negative voltage supply. Each current source may be electrically coupled to its corresponding electrode by way of a common node. For example, with respect to a particular electrode included in the plurality of electrodes, a positive current source and a negative current source may both be electrically coupled to the electrode by way of a common node. In this configuration, the sound processor may 1) direct the cochlear implant to concurrently enable the positive and negative current sources corresponding to the electrode in order to generate a current that has a predetermined current level and that flows though the positive and negative current sources from the positive voltage supply to the negative voltage supply without providing stimulation to the electrode in a manner perceptible to the patient, and 2) determine a power level of the RF power that is required to generate the current having the predetermined current level.

The systems and methods described herein may advantageously allow for creation of an active load during operation of the cochlear implant system. In other words, the current sources themselves (as opposed to an electrode and/or patient tissue in the vicinity of the electrode) may be used as the load when determining a power level of RF power required to generate current having a particular current level. The active load may be used to determine an RF power level required to generate a range of predetermined different current levels. In this manner, a table showing or defining a relationship between RF power levels and current may be generated and then used to select and/or optimize future RF power levels to output to the cochlear implant. Advantageously, the required RF power levels may be determined in a manner that is transparent to the patient (i.e., in a manner that does not provide perceptible stimulation to the patient). The systems and methods described herein may also result in improved battery life for the cochlear implant system because the information included in the generated table may be used to dynamically adjust the RF power level to an optimal level based on the current needs of the cochlear implant (e.g., by adjusting the RF power level to a minimum level that allows for generation of a particular current level). Other benefits of the systems and methods described herein will be made apparent herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or RF power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or RF power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112. For ease of explanation, the following description refers to one of the electrodes included in electrodes 112. It will be understood that the impedance for any and all of the electrodes included in electrodes 112 may be separately determined according to principles described herein.

Figure 2:
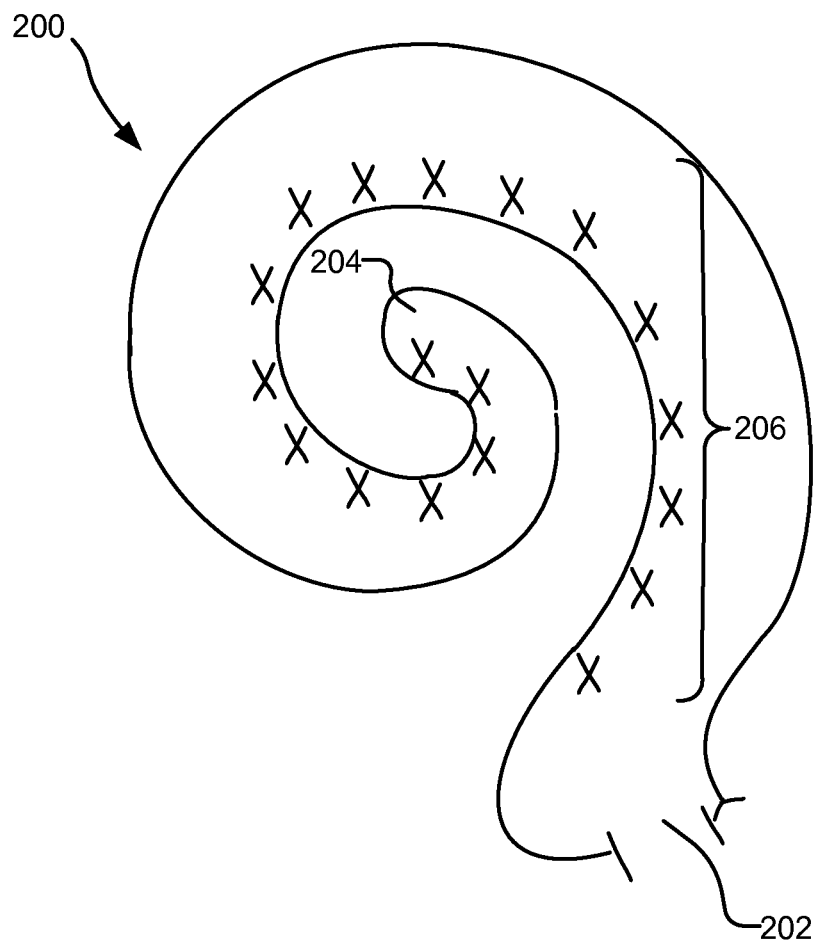
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
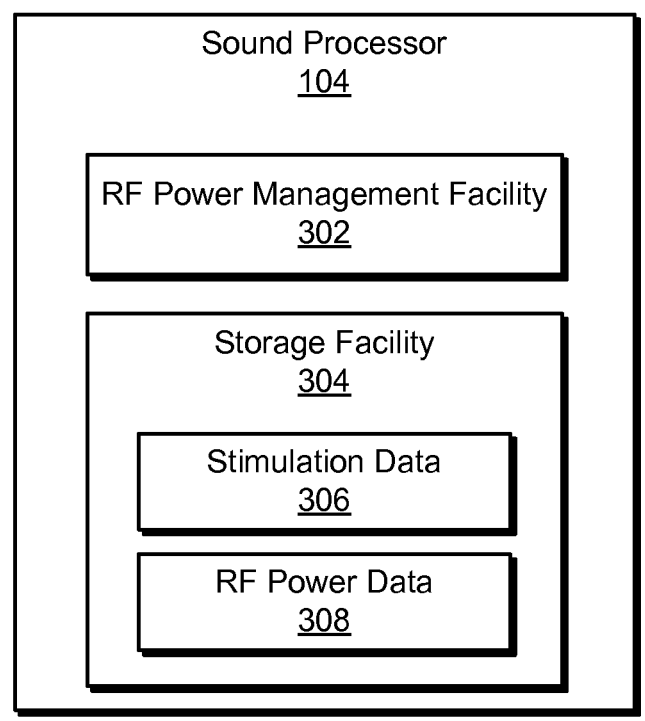
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include an RF power management facility 302 and a storage facility 304, which may be in communication with one another using any suitable communication technologies. Storage facility 304 may be configured to maintain stimulation data 306 generated and/or used by RF power management facility 302, and RF power data 308 measured and/or used by RF power management facility 302. Storage facility 306 may maintain additional or alternative data as may serve a particular implementation. One or more of facilities 302 and 304 may include a computing device or processor configured to perform one or more of the functions described herein. Facilities 302 and 304 will now be described in more detail.

RF power management facility 302 may be configured to perform various RF power management operations. For example, RF power management facility 302 may perform one or more operations in which RF power management facility 302 determines how much RF power (e.g., a power level of an RF signal coming from headpiece 106 via communication link 114) is required to generate various current levels associated one or more of the electrodes included in the plurality of electrodes 112. To this end, RF power management facility 302 may create an active load in cochlear implant 108.

Figure 4:
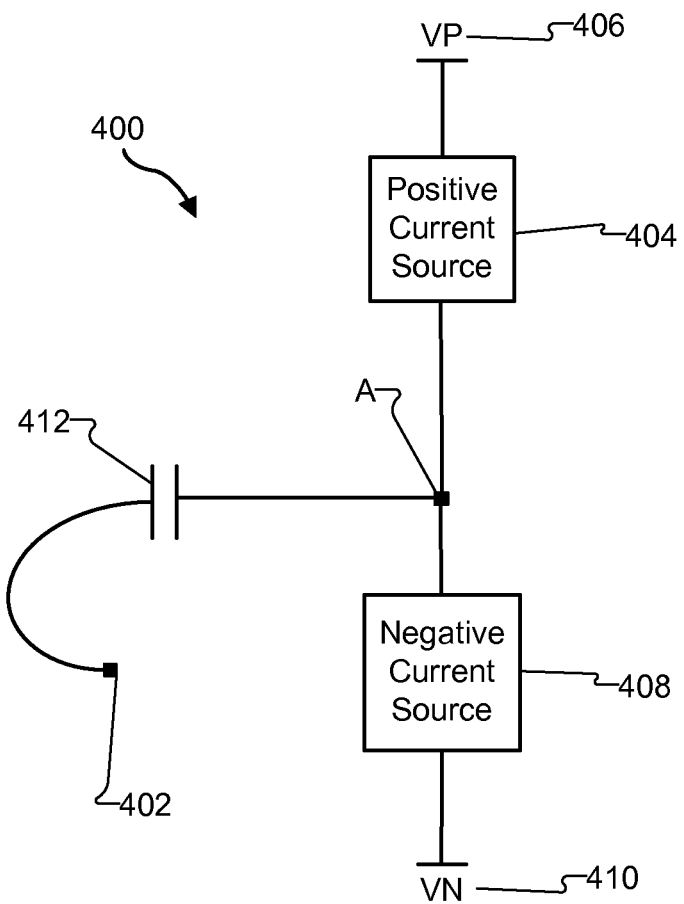
FIG. 4 illustrates an exemplary current generation circuit according to the principles described herein.

To illustrate, FIG. 4 shows an exemplary current generation circuit 400 associated with a particular electrode 402 (which may be one of electrodes 112, for example) and that may be included within cochlear implant 108. A similar current generation circuit 400 may be included within cochlear implant 108 for each electrode included in electrodes 112. Current generation circuit 400 may operate (e.g., generate current) in accordance with RF power provided by sound processor 104 in any suitable manner.

As shown in FIG. 4, current generation circuit 400 may include a positive current source 404 tied to a positive voltage supply 406 (labeled "VP" in FIG. 4) and a negative current source 408 tied to a negative voltage supply 410 (labeled "VN" in FIG. 4). It will be recognized that the current generation circuit components shown in FIG. 4 are merely representative of the many different components that may be included in current generation circuit 400 and that current generation circuit 400 may include additional or alternative components as may serve a particular implementation. When not being used by RF power management facility 302 to determine RF power levels, positive current source 404 and negative current source 408 may be configured to generate an electrical stimulation pulse that may represent an audio signal and that may be applied to a patient (e.g., to a location within the cochlea of the patient) by way of electrode 402 and a DC blocking capacitor 412. As illustrated in FIG. 4, positive current source 404 and negative current source 408 may be electrically coupled to electrode 402 by way of a node A.

To create an active load in cochlear implant 108, RF power management facility 302 may concurrently enable both positive current source 404 and negative current source 408. The enabled current sources 404 and 408 may serve as an active load for the current generated by current sources 404 and 408. In other words, current may flow from positive voltage supply 406 to negative voltage supply 410 through both current sources 404 and 408.

Returning to FIG. 3, RF power management facility 302 may determine a relationship between RF power and various levels of current associated with electrode 402. In other words, RF power management facility 302 may determine various RF power levels that are required to generate and apply various current levels to electrode 402. This determination may be performed during, for example, an initialization of the sound processor 104. In conventional cochlear implant systems, a process of determining a relationship between required RF power and current levels involves providing at least some stimulation current to the electrode during an internal loading sequence, which results in the patient experiencing an undesirable perception of a noise.

To avoid such an undesirable effect, RF power management facility 302 may direct cochlear implant 108 to concurrently enable positive current source 404 and negative current source 408 in order to generate a current that has a predetermined current level and that flows through the positive and negative current sources 404 and 408 from positive voltage supply 406 to negative voltage supply 410. For example, RF power management facility 302 may direct cochlear implant 108 to concurrently generate a first current with positive current source 404 and a second current with negative current source 408. The first and second currents may be equal in amplitude and pulse width so that they combine to result in the single current having the predetermined current level.

As described above, concurrent enabling of the positive and negative current sources 404 and 408 may create an active load in the cochlear implant 108, and as such, may prevent current from flowing to electrode 402. In this manner, the current does not create stimulation of the electrode 402 that is perceptible to the patient. It will be recognized that, in some examples, the positive and negative current sources 404 and 408 may be slightly mismatched, thus resulting in a relatively small amount of current flowing through electrode 402. However, this relatively small amount of current may not be of sufficient amplitude to create a perceptible stimulation event. Moreover, in some examples, any mismatched current may be detected and compensated for in order to prevent or minimize the amount of current that is applied to electrode 402.

After concurrently enabling positive current source 404 and negative current source 408, RF power management facility 302 may determine a power level (e.g., a minimum power level) of the RF power provided by sound processor 104 that is required to generate the current having the predetermined current level. This may be performed in any suitable manner, as will be described in more detail below.

Data representative of the determined RF power level may be stored and associated with the predetermined current level by RF power management facility 302. This may be performed in any suitable manner. For example, RF power management facility 302 may include data representative of the determined power level and the predetermined current level in a table (e.g., a POEM table). The table may be stored in the form of any suitable data structure as may serve a particular implementation.

RF power management facility 302 may repeat the process described above to determine RF power levels required to generate and apply a range of current levels to electrode 402. For example, RF power management facility 302 may determine n different RF power levels that are required to generate n different current levels, where n is any suitable integer greater than zero.

Figure 5:
FIG. 5 illustrates an exemplary table showing RF power levels and corresponding current levels according to principles described herein.

In some examples, RF power management facility 302 may utilize the determined RF power levels to generate a table (e.g., a POEM table) that shows a relationship between RF power levels and current levels that may be applied to a particular electrode. To illustrate, FIG. 5 shows an exemplary table 500 that may be generated by RF power management facility 302. As shown in FIG. 5, table 500 indicates that an RF power level equal to $P_1$ is required to generate a current level of $i_1$, an RF power level equal to $P_2$ is required to generate a current level of $i_2$, and so forth up to an RF power level $P_N$ and a corresponding current level $i_N$.

RF power management facility 302 may generate table 500 in any suitable manner. To illustrate, RF power management facility 302 may generate table 500 by incrementally varying an amplitude of the current that is concurrently provided via positive current source 404 and negative current source 408 to determine the RF power requirements of the cochlear implant 108 at the different incremental current levels. For example, RF power management facility 302 may first direct cochlear implant 108 to generate current having a current level of 100 microamps by concurrently directing positive and negative current sources 404 and 408 to each generate 50 microamps of current. RF power management facility 302 may then adjust the RF power level provided by sound processor 104 until a minimum RF power level that allows the generation of the 100 microamp current. This RF power level may then be designated as the RF power level that is required to generate the 100 microamp current. RF power management facility 302 may subsequently perform the same process for current levels of 200 microamps, 300 microamps, etc. It will be recognized that the incremental step sizes may vary as may serve a particular implementation.

In some examples, table 500 may be used by RF power management facility 302 to adjust and/or optimize power levels of RF power to be provided to cochlear implant 108. For example, during a normal operation of cochlear implant 108 (i.e., while cochlear implant 108 is being used to apply electrical stimulation representative of audio content presented to the patient), RF power management facility 302 may optimize (e.g., minimize) an amount of RF power provided to cochlear implant 108 based on the relationships shown in table 500.

For example, RF power management facility 302 may reduce an amount of RF power provided to cochlear implant 108 if table 500 indicates that only a certain amount of RF power is required to generate a desired current level. In this manner, RF power management facility 302 may reduce power consumption by the cochlear implant 108 and, as a result, maximize the life of a battery associated with cochlear implant system 100.

The above description explains how RF power management facility 302 may determine a relationship between RF power and current levels associated with electrode 402. In some examples, RF power management facility 302 may separately determine the relationships between RF power and current levels associated with each of the electrodes included in a plurality of electrodes (e.g., electrodes 112) coupled to cochlear implant 108. In addition, RF power management facility 302 may generate a table similar to that illustrated in FIG. 5 for each of the electrodes included in the plurality of electrodes.

Figure 6:
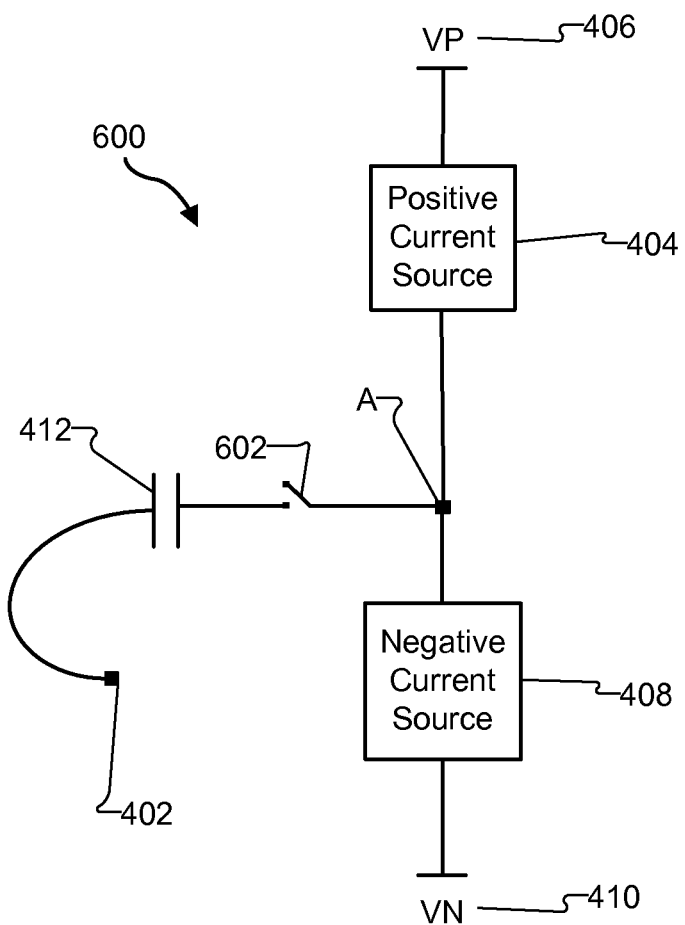
FIG. 6 illustrates another exemplary current generation circuit according to principles described herein.

FIG. 6 shows another exemplary current generation circuit 600 that may be included in cochlear implant 108. Current generation circuit 600 is similar to current generation circuit 400 except that, in current generation circuit 600, a switch 602 is provided in series between node A and electrode 402. RF power management facility may direct cochlear implant 108 to direct switch 602 to be in an open state while positive current source 404 and negative current source 408 are concurrently enabled. In this manner, switch 602 may ensure that current does not flow to electrode 402 (and thereby prevent any perception by the user of the current). Switch 602 may be implemented in any suitable manner as may suit a particular implementation. For example, switch 602 may be implemented by a physical switch and/or any suitable software component.

Figure 7:
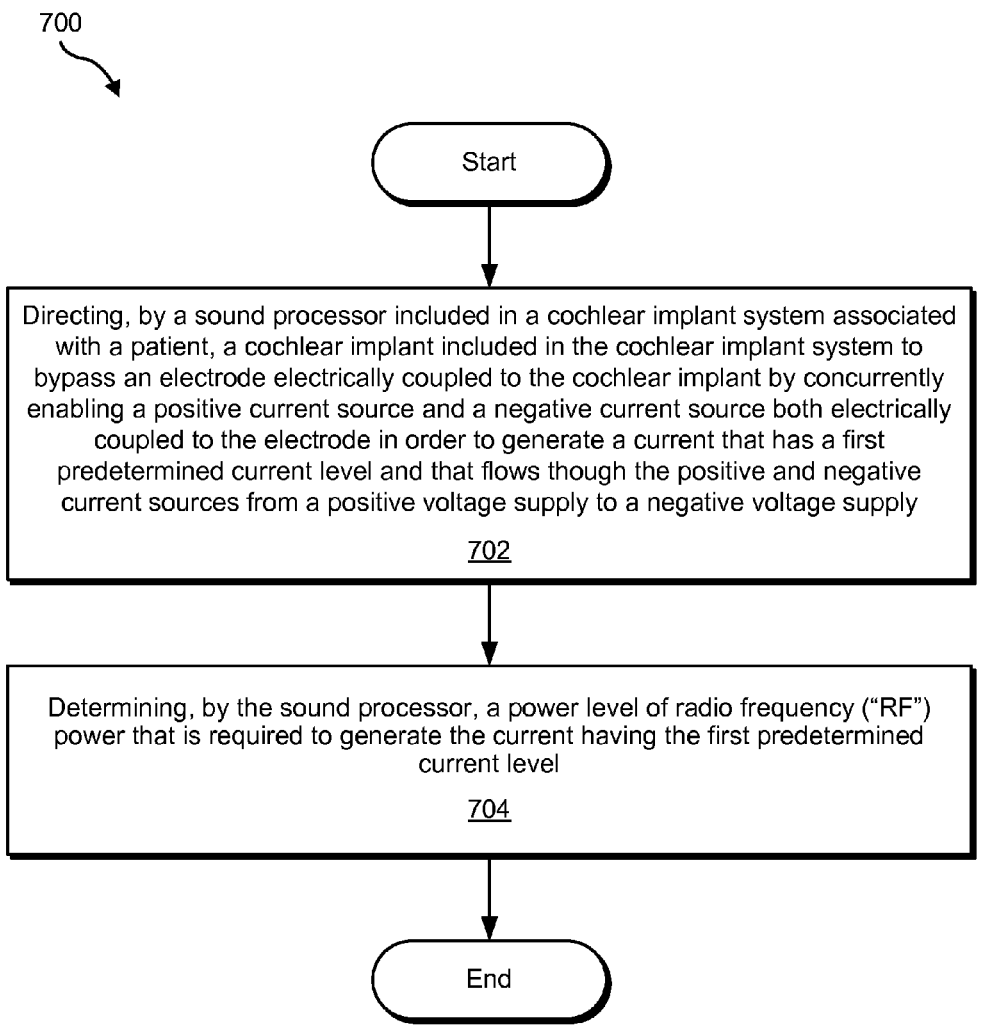
FIG. 7 illustrates an exemplary RF power level management method according to principles described herein.

FIG. 7 illustrates an exemplary RF power level management method. While FIG. 7 illustrates exemplary steps according to one embodiment, other embodiments may omit, add to, reorder, and/or modify any of the steps shown in FIG. 7. One or more of the steps shown in FIG. 7 may be performed by sound processor 104 and/or any implementation thereof.

In step 702, a sound processor, included in a cochlear implant system associated with a patient, directs a cochlear implant included in the cochlear implant system to bypass an electrode electrically coupled to the cochlear implant by concurrently enabling a positive current source and a negative current source both electrically coupled to the electrode in order to generate a current that has a first predetermined current level and that flows though the positive and negative current sources from a positive voltage supply to a negative voltage supply. Step 702 may be performed in any of the ways described herein.

In step 704, the sound processor determines a power level of radio frequency ("RF") power that is required to generate the current having the first predetermined current level. Step 704 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sound processor that provides radio frequency ("RF") power; and
a cochlear implant that operates in accordance with the RF power provided by the sound processor and that is electrically coupled to a plurality of electrodes, the cochlear implant being implanted within a patient and including a positive current source tied to a positive voltage supply and a negative current source tied to a negative voltage supply, wherein the positive and negative current sources are electrically coupled to an electrode included in the plurality of electrodes by way of a common node;
wherein the sound processor
directs the cochlear implant to concurrently enable the positive and negative current sources in order to generate a current that has a first predetermined current level and that flows though the positive and negative current sources from the positive voltage supply to the negative voltage supply without providing stimulation to the electrode in a manner perceptible to the patient, the concurrently enabling of the positive and negative current sources creating an active load in the cochlear implant, and determines a power level of the RF power that is required to generate the current having the first predetermined current level.

2. The system of claim 1, wherein the sound processor adjusts the RF power provided to the cochlear implant based at least in part on the determined power level of the RF power that is required to generate the current having the first predetermined current level.

3. The system of claim 1, wherein:
the current generated by concurrently enabling the positive and negative current sources includes a first current from the positive current source and a second current from the negative current source, and
the first current and the second current are substantially equal in amplitude and pulse width.

4. The system of claim 1, wherein:
the sound processor, subsequent to determining the power level of the RF power that is required to generate the current having the first predetermined current level,
directs the cochlear implant to concurrently enable the positive and negative current sources in order to generate an additional current that has a second predetermined current level and that flows though the positive and negative current sources from the positive voltage supply to the negative voltage supply without providing stimulation to the electrode in a manner perceptible to the patient, and
determines an additional power level of the RF power that is required to generate the additional current having the second predetermined current level.

5. The system of claim 4, wherein the sound processor generates a table showing a relationship between RF power levels and current levels based on the determined power level, the first predetermined current level, the determined additional power level, and the second predetermined current level.

6. The system of claim 5, wherein the sound processor optimizes an amount of RF power provided to the cochlear implant during a normal operation of the cochlear implant based on the relationship shown in the table.

7. The system of claim 1, wherein:
the cochlear implant further includes a switch in series between the common node and the electrode; and
the sound processor directs the switch to be in an open state while the positive and negative current sources are concurrently enabled.

8. A cochlear implant implanted within a patient and that operates in accordance with radio frequency ("RF") power provided by a sound processor, the cochlear implant comprising:
a positive current source tied to a positive voltage supply and a negative current source tied to a negative voltage supply, the positive and negative current sources being electrically coupled to an electrode included in a plurality of electrodes by way of a common node; and
control circuitry coupled to the positive and negative current sources and that
receives an instruction from the sound processor, and
concurrently enables, based on the instruction received from the sound processor, the positive and negative current sources in order to generate a current that has a first predetermined current level and that flows though the positive and negative current sources from the positive voltage supply to the negative voltage supply without providing stimulation to the electrode in a manner perceptible to the patient,
wherein the concurrently enablement of the positive and negative current sources creates an active load in the cochlear implant.

9. The cochlear implant of claim 8, wherein, subsequent to generating the current that has the first predetermined current level, the control circuitry
receives an additional instruction from the sound processor, and
concurrently enables, based on the additional instruction from the sound processor, the positive and negative current sources in order to generate an additional current that has a second predetermined current level and that flows though the positive and negative current sources from the positive voltage supply to the negative voltage supply without providing stimulation to the electrode in a manner perceptible to the patient.

10. The cochlear implant of claim 9, wherein the cochlear implant receives, from the sound processor, an adjusted amount of RF power based on a relationship between the first predetermined current level and the power level and a relationship between the second predetermined current level and the additional power level.

11. The cochlear implant of claim 8, further comprising a switch provided between the common node and the electrode, wherein the control circuitry causes the switch to be in an open state while the positive and negative current sources are concurrently enabled.

12. The cochlear implant of claim 8, wherein:
the current generated by enabling the positive and negative current sources includes a first current from the positive current source and a second current from the negative current source, and
the first current and the second current are equal in amplitude and pulse width.

13. A method comprising:
directing, by a sound processor included in a cochlear implant system associated with a patient, a cochlear implant included in the cochlear implant system to bypass an electrode electrically coupled to the cochlear implant by concurrently enabling a positive current source and a negative current source both electrically coupled to the electrode in order to generate a current that has a first predetermined current level and that flows though the positive and negative current sources from a positive voltage supply to a negative voltage supply, the concurrently enabling of the positive and negative current sources creating an active load in the cochlear implant; and
determining, by the sound processor, a power level of radio frequency ("RF") power that is required to generate the current having the first predetermined current level.

14. The method of claim 13, wherein the cochlear implant bypasses the electrode without providing stimulation to the electrode in a manner perceptible to the patient.

15. The method of claim 13, wherein:
the current generated by enabling the positive and negative current sources includes a first current from the positive current source and a second current from the negative current source, and
the first current and the second current are equal in amplitude and pulse width.

16. The method of claim 13, further comprising:
directing, by the sound processor, the cochlear implant included in the cochlear implant system to again bypass the electrode electrically coupled to the cochlear implant by again concurrently enabling the positive and negative current sources electrically coupled to the electrode in order to generate an additional current that has a second predetermined current level and that flows though the positive and negative current sources from the positive voltage supply to the negative voltage supply; and
determining, by the sound processor, an additional power level of the RF power that is required to generate the additional current having the second predetermined current level.

17. The method of claim 16, further comprising optimizing, by the sound processor, an amount of RF power provided to the cochlear implant based a relationship between the first predetermined current level and the determined power level and a relationship between the second predetermined current level and the determined additional power level.

18. The method of claim 16, further comprising generating, by the sound processor, a table showing a relationship between RF power levels and current levels based on the determined power level, the first predetermined current level, the determined additional power level, and the second predetermined current level.

19. The method of claim 18, further comprising optimizing, by the sound processor, an amount of RF power provided to the cochlear implant during a normal operation of the cochlear implant based on the relationship shown in the table.

* * * * *